United States Patent
Chopra et al.

(10) Patent No.: US 11,723,606 B2
(45) Date of Patent: Aug. 15, 2023

(54) SYSTEMS AND METHODS FOR ANATOMIC MOTION COMPENSATION

(71) Applicant: INTUITIVE SURGICAL OPERATIONS, INC., Sunnyvale, CA (US)

(72) Inventors: Prashant Chopra, Foster City, CA (US); Vincent Duindam, San Francisco, CA (US); Caitlin Q. Donhowe, Mountain View, CA (US); Tao Zhao, Sunnyvale, CA (US); Timothy D. Soper, San Jose, CA (US); Federico Barbagli, San Francisco, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 218 days.

(21) Appl. No.: 17/127,888

(22) Filed: Dec. 18, 2020

(65) Prior Publication Data

US 2021/0106289 A1   Apr. 15, 2021

Related U.S. Application Data

(63) Continuation of application No. 14/665,650, filed on Mar. 23, 2015, now Pat. No. 10,912,523.
(Continued)

(51) Int. Cl.
*A61B 5/00* (2006.01)
*A61B 5/06* (2006.01)
(Continued)

(52) U.S. Cl.
CPC ........ *A61B 5/7425* (2013.01); *A61B 1/00006* (2013.01); *A61B 1/000094* (2022.02);
(Continued)

(58) Field of Classification Search
CPC .... A61B 2030/2061; A61B 2034/2051; A61B 5/065; A61B 5/062; A61B 34/20;
(Continued)

(56) References Cited

U.S. PATENT DOCUMENTS 6,380,732 B1   4/2002  Gilboa
6,389,187 B1   5/2002  Greenaway et al.
(Continued)

FOREIGN PATENT DOCUMENTS

WO   WO-2009097461 A1 *  8/2009   ........... A61B 1/0051

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Ashley K Buran
*Assistant Examiner* — Helene Bor
(74) *Attorney, Agent, or Firm* — Haynes and Boone, LLP

(57) ABSTRACT

A medical system includes an interventional instrument and a control system including one or more processors. The control system is configured to: receive a pose dataset for a point on the instrument retained in compliant movement with a cyclically moving patient anatomy for a plurality of time parameters during a cyclical anatomical motion; determine a set of pose differentials for the identified point with respect to a reference point at each time parameter; identify a periodic signal for the anatomical motion from the set of pose differentials; generate a command signal indicating an intended movement of the instrument relative to the patient anatomy; adjust the command signal to include an instruction for a cyclical instrument motion based on a phase of the anatomical motion; and cause the intended movement of the instrument relative to the patient anatomy based on the
(Continued)

adjusted command signal to compensate for the anatomical motion.

16 Claims, 8 Drawing Sheets

Related U.S. Application Data

(60) Provisional application No. 62/052,802, filed on Sep. 19, 2014, provisional application No. 61/969,510, filed on Mar. 24, 2014.

(51) Int. Cl.
| | |
|---|---|
| *A61B 34/20* | (2016.01) |
| *A61B 1/00* | (2006.01) |
| *A61B 1/045* | (2006.01) |
| *A61B 17/00* | (2006.01) |
| *A61B 1/267* | (2006.01) |
| *A61B 1/05* | (2006.01) |

(52) U.S. Cl.
CPC .............. *A61B 1/045* (2013.01); *A61B 5/062* (2013.01); *A61B 5/065* (2013.01); *A61B 34/20* (2016.02); *A61B 1/00165* (2013.01); *A61B 1/00193* (2013.01); *A61B 1/05* (2013.01); *A61B 1/2676* (2013.01); *A61B 5/06* (2013.01); *A61B 5/7285* (2013.01); *A61B 2017/00699* (2013.01); *A61B 2034/2051* (2016.02); *A61B 2034/2061* (2016.02)

(58) Field of Classification Search
CPC .................... A61B 1/00; A61B 5/7425; A61B 2017/00699; A61B 5/06; A61B 1/2676; A61B 1/05; A61B 1/00193; A61B 1/045; A61B 1/00165; A61B 1/00009; A61B 1/00006

See application file for complete search history.

(56) References Cited

U.S. PATENT DOCUMENTS

| | | | |
|---|---|---|---|
| 6,675,040 B1 | 1/2004 | Cosman | |
| 6,892,090 B2 | 5/2005 | Verard et al. | |
| 7,772,541 B2 | 8/2010 | Froggatt et al. | |
| 7,781,724 B2 | 8/2010 | Childers et al. | |
| 7,930,065 B2 | 4/2011 | Larkin et al. | |
| 8,295,909 B2 | 10/2012 | Goldbach et al. | |
| 2005/0197559 A1* | 9/2005 | Boese | A61B 5/7207 600/407 |
| 2006/0013523 A1 | 1/2006 | Childers et al. | |
| 2006/0058647 A1* | 3/2006 | Strommer | A61B 6/12 600/434 |
| 2007/0066881 A1 | 3/2007 | Edwards et al. | |
| 2008/0118135 A1* | 5/2008 | Averbuch | G06T 7/155 382/131 |
| 2010/0174178 A1 | 7/2010 | Edwards et al. | |
| 2011/0019878 A1* | 1/2011 | Soubelet | G06T 7/246 382/128 |
| 2012/0289777 A1* | 11/2012 | Chopra | A61B 1/00055 382/128 |
| 2012/0289843 A1* | 11/2012 | Chopra | A61B 1/009 600/595 |
| 2013/0303890 A1 | 11/2013 | Duindam et al. | |
| 2013/0303894 A1 | 11/2013 | Duindam et al. | |
| 2014/0088377 A1* | 3/2014 | Manzke | A61B 5/1073 600/595 |
| 2015/0265368 A1 | 9/2015 | Chopra et al. | |

\* cited by examiner

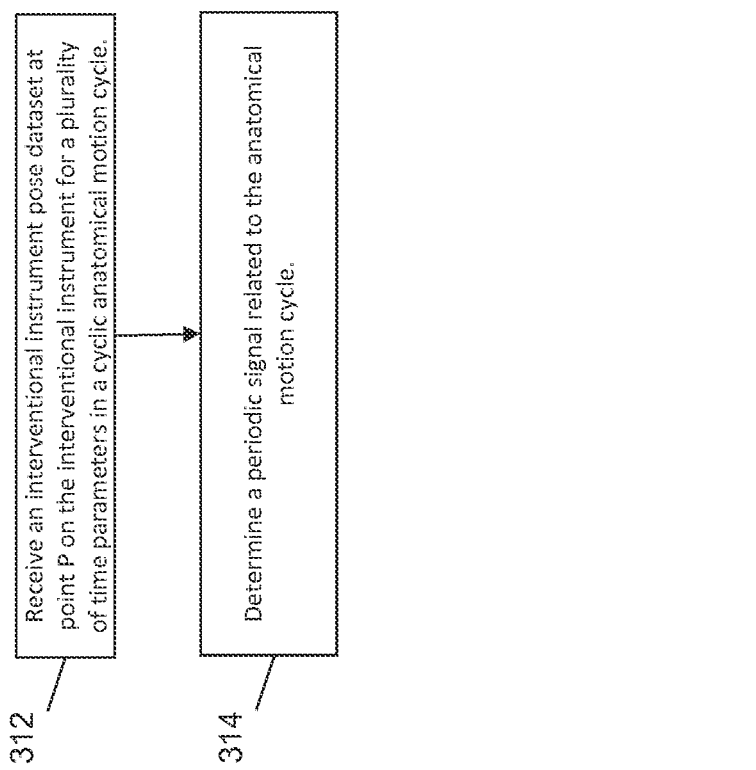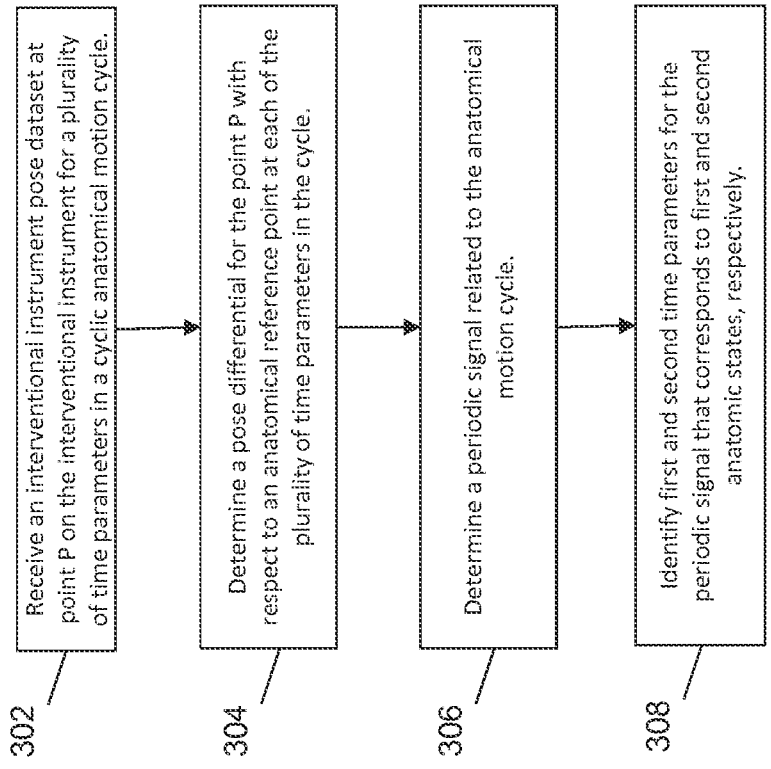

FIG. 7

| | 600 |
|---|---|
| Location 1 | Motion Measurement A |
| Location 2 | Motion Measurement B |
| Location 3 | Motion Measurement C |
| Location 4 | Motion Measurement D |
| Location 5 | Motion Measurement E |
| Location 6 | Motion Measurement F |

| | 610 |
|---|---|
| Location 1 | Set A |
| Location 2 | Set B |
| Location 3 | Set C |
| Location 4 | Set D |
| Location 5 | Set E |
| Location 6 | Set F |

612 — 614

SYSTEMS AND METHODS FOR ANATOMIC MOTION COMPENSATION

RELATED APPLICATIONS

This patent application is a continuation of U.S. application Ser. No. 14/665,650 filed Mar. 23, 2015, which claims priority to and the benefit of the filing date of U.S. Provisional Patent Applications 61/969,510 entitled "Systems and Methods for Anatomic Motion Compensation to Register Interventional Instruments," filed Mar. 24, 2014 and of U.S. Provisional Patent Application 62/052,802, entitled "Systems and Methods for Anatomic Motion Compensation," filed. Sep. 19, 2014, which are incorporated by, reference herein in their entire.

FIELD

The present disclosure is directed to systems and methods for navigating a patient anatomy to conduct a minimally invasive procedure, and more particularly to systems and methods for dynamically deforming an anatomical passageway model for display.

BACKGROUND

Minimally invasive medical techniques are intended to reduce the amount of tissue that is damaged during interventional procedures, thereby reducing patient recovery time, discomfort, and harmful side effects. Such minimally invasive techniques may be performed through natural orifices in a patient anatomy or through one or more surgical incisions. Through these natural orifices or incisions clinicians may insert interventional instruments (including surgical, diagnostic, therapeutic, or biopsy instruments) to reach a target tissue location. To reach the target tissue location, a minimally invasive interventional instrument may navigate natural or surgically created passageways in anatomical systems such as the lungs, the colon, the intestines, the kidneys, the heart, the circulatory system, or the like. Teleoperated interventional systems may be used to insert and position the interventional instrument within the patient anatomy, During navigation of the interventional instrument, the clinician may be assisted by receiving preoperative or intraoperative images of the patient anatomy registered with the position of the interventional instrument. Many regions of the patient anatomy are dynamic in normal function (e.g., heart, lungs, kidneys, liver, blood vessels). Conventional methods of registering an interventional instrument with images of a dynamic anatomy are inadequate in some ways. For example, conventional methods of registration using electromagnetic (EM) sensors attempt to time sensing measurements at baseline conditions (e.g. full exhalation, full inhalation). However, taking such measurements precisely in synchronization with the baseline condition leads to inconsistencies between perceived and actual instrument positions. Furthermore, the discontinuous nature of the baseline-only measurements may provide a jerky, non-intuitive experience for the clinician viewing displayed images of the registration. Systems and methods are needed for improved registration of an interventional instrument with images of a dynamic anatomy.

SUMMARY

The embodiments of the invention are summarized by the claims that follow the description.

In one embodiment, a method of modeling a cyclic anatomical motion comprises receiving a pose dataset for an identified point on an interventional instrument retained within and in compliant movement with a cyclically moving patient anatomy for a plurality of time parameters. The method also includes determining a set of pose differentials for the identified point with respect to a reference point at each of the plurality of time parameters and identifying a periodic signal for the cyclic anatomical motion from the set of pose differentials.

In another embodiment, a method of tracking an interventional instrument within a plurality of passageways of a patient anatomy during cyclical anatomical motion comprises receiving a set of image data representing the plurality of passageways at a first cyclical motion state and receiving a set of image data representing the plurality of passageways at a second cyclical motion state. The method also includes receiving pose data for a plurality of points describing a shape of an interventional instrument positioned with the plurality of passageways at a first time parameter and comparing the shape of the interventional instrument at the first time parameter to the sets of image data representing the plurality of passageway's at the first and second cyclical motion states. The method further includes assigning a match score to each of the sets of image data and determining a selected set of image data for the best match score.

In another embodiment, a method of tracking a cyclic anatomical motion comprises receiving a pose dataset for an identified point on an interventional instrument retained within and in compliant movement with a cyclically moving patient anatomy for a plurality of time parameters and identifying a periodic signal for the cyclic anatomical motion. The cyclical anatomical motion is respiration.

Additional aspects, features, and advantages of the present disclosure will become apparent from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 3a illustrates a method for modeling cyclic anatomical motion according to an embodiment of this disclosure.

FIG. 3b illustrates a method for modeling cyclic anatomical motion according to another embodiment of this disclosure.

FIGS. 7 and 8 illustrate look-up tables according to different embodiments of the present disclosure.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an elongated object.

Figure 1:
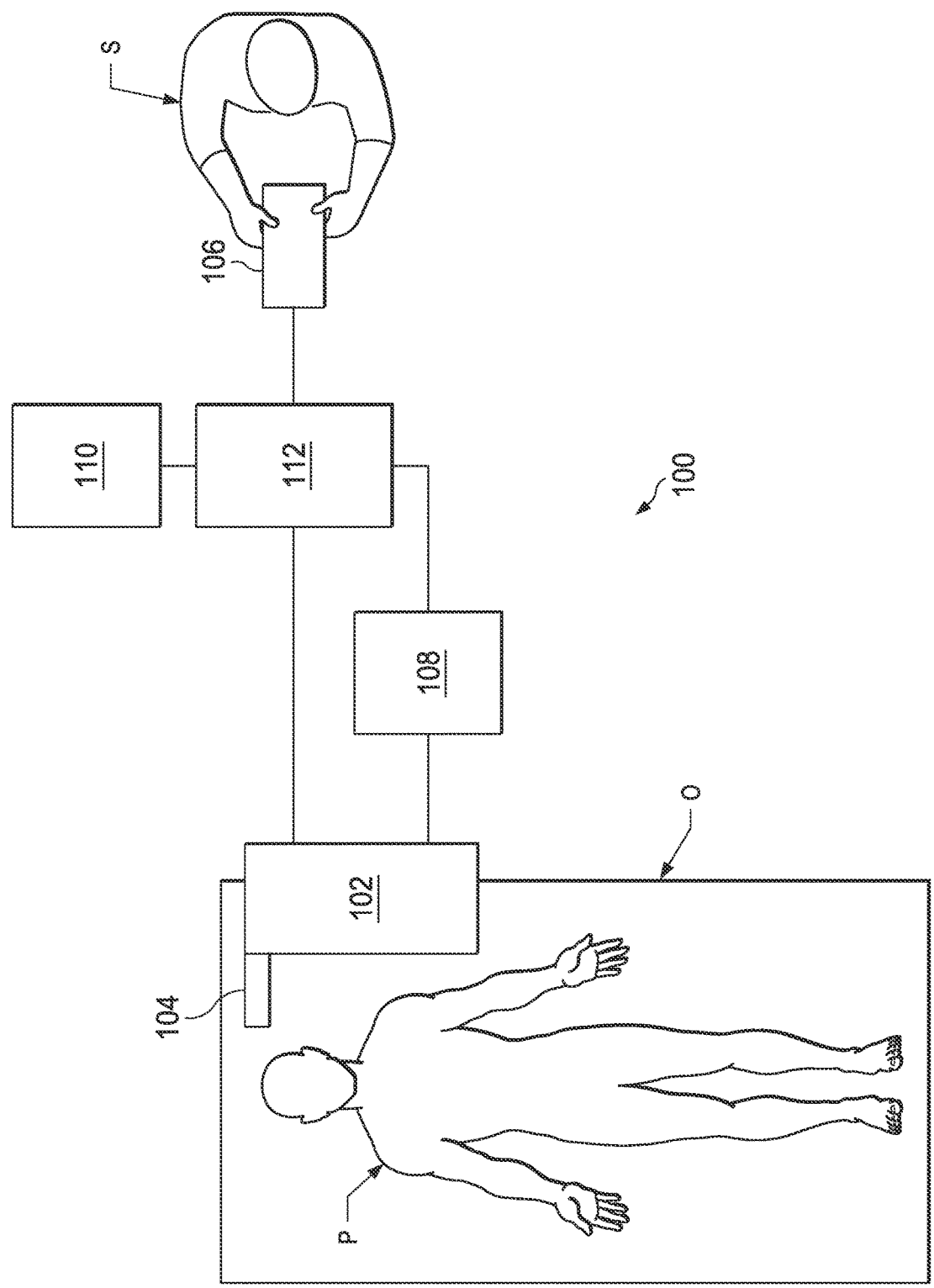
FIG. 1 is a telerobotic interventional system, in accordance with an embodiment of the present disclosure.

Referring to FIG. 1 of the drawings, a telerobotic interventional system for use in, for example, surgical, diagnostic, therapeutic, or biopsy procedures, is generally indicated by the reference numeral 100. As will be described, the telerobotic interventional systems of this disclosure are generally under the teleoperational control of a surgeon. However, for some procedures or sub-procedures, the telerobotic interventional system may be under the partial or full control of a computer programmed to perform the procedure or sub-procedure. As shown in FIG. 1, the telerobotic interventional system 100 generally includes a robotic assembly 102 mounted to or near an operating table O on which a patient P is positioned. An interventional instrument system 104 is operably coupled to the robotic assembly 102. An operator input system 106 allows a surgeon or other type of clinician S to view the surgical site and to control the operation of the interventional instrument system 104.

The operator input system 106 may be located at a surgeon's console which is usually located in the same room as operating table O. However, it should be understood that the surgeon S can be located in a different room or a completely different building from the patient P. Operator input system 106 generally includes one or more control device(s) for controlling the interventional instalment system 104. The control device(s) may include any number of a variety of input devices, such as hand grips, joysticks, trackballs, data gloves, trigger-guns, hand-operated controllers, voice recognition devices, touch screens, body motion or presence sensors, or the like. In some embodiments, the control device(s) will be provided with the same degrees of freedom as the interventional instruments of the robotic assembly to provide the surgeon with telepresence, or the perception that the control device(s) are integral with the instruments so that the surgeon has a strong sense of directly controlling instruments. In other embodiments, the control device(s) may have more or fewer degrees of freedom than the associated interventional instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, or the like).

The robotic assembly 102 supports the interventional instrument system 104 and may comprise a kinematic structure of one or more non-servo controlled links (e.g., one or more links that may be manually positioned and locked in place, generally referred to as a set-up structure) and a robotic manipulator. The robotic assembly 102 includes plurality of actuators (e.g., motors) that drive inputs on the interventional instrument 104. These motors actively move in response to commands from the control system (e.g., control system 112). The motors include drive systems which when coupled to the interventional instrument 104 may advance the interventional instrument into a naturally or surgically created anatomical orifice and/or may move the distal end of the interventional instrument in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, the motors can be used to actuate an articulable end effector of the instrument for grasping tissue in the jaws of a biopsy device or the like.

The robotic interventional system 100 also includes a sensor system 108 with one or more sob-systems for receiving information about the instruments of the robotic assembly. Such sub-systems may include a position sensor system (e.g., an electromagnetic (EM) sensor system); a shape sensor system for determining the position, orientation, speed, pose, and/or shape of the catheter tip and/or of one or more segments along a flexible body of instrument 104; and/or a visualization system for capturing images from the distal end of the catheter system.

The robotic interventional system 100 also includes a display system 110 for displaying an image of the surgical site and interventional instruments 104 generated by sub-systems of the sensor system 108. The display 110 and the operator input system 106 may be oriented so the operator can control the interventional instrument system 104 and the operator input system 106 as if viewing the workspace in substantially true presence. True presence means that the displayed tissue image appears to an operator as if the operator was physically present at the image location and directly viewing the tissue from the perspective of the image.

Alternatively or additionally, display system 110 may present images of the surgical site recorded and/or imaged preoperatively or intra-operatively using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. The presented preoperative or intra-operative images may include two-dimensional, three-dimensional, or four-dimensional (including e.g., time based or velocity based information) images and associated image data sets for reproducing the images.

In some embodiments, the display system 110 may display a virtual visualization image in which the actual location of the interventional instrument is registered (e.g., dynamically referenced) with preoperative or concurrent images to present the surgeon with a virtual image of the internal surgical site at the location of the tip of the surgical instrument.

In other embodiments, the display system 110 may display a virtual visualization image in which the actual location of the interventional instrument is registered with prior images (including preoperatively recorded images) or concurrent images to present the surgeon with a virtual image of an interventional instrument at the surgical site. An image of a portion of the interventional instrument 104 may be superimposed on the virtual image to assist the surgeon controlling the interventional instrument.

The robotic interventional system 100 also includes a control system 112. The control system 112 includes at least one memory and at least one processor (not shown), and typically a plurality of processors, for effecting control between the interventional instrument system 104, the operator input system 106, the sensor system 108, and the display system 110. The control system 112 also includes programmed instructions (e.g., a computer-readable medium storing the instructions) to implement some or all of the methods described herein. While control system 112 is shown as a single block in the simplified schematic of FIG. 1, the system may comprise a number of data processing circuits with a portion of the processing optionally being performed on or adjacent the robotic assembly 102, a portion being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the robotic systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers to provide force and torque feedback from the interventional instrument system 104 to one or more corresponding servomotors for the operator input system 106. The servo controller(s) may also transmit signals instructing robotic assembly 102 to move the interventional instruments 104 which extend into an internal surgical site within the patient body via openings in the body. Any suitable conventional or specialized servo controller may be used. A servo controller may be separate from, or integrated with, robotic assembly 102. In some embodiments, the servo controller and robotic assembly are provided as part of a robotic arm cart positioned adjacent to the patient's body.

The control system 112 may further include a virtual visualization system to provide navigation assistance to the interventional instruments 104. Virtual navigation using the virtual visualization system is based upon reference to an acquired dataset associated with the three dimensional structure of the anatomical passageways. More specifically, the virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software is used to convert the recorded images into a two dimensional or three dimensional composite representation of a partial or an entire anatomical organ or anatomical region. An image data set is associated with the composite representation. The composite representation and the image data set describe the various locations and shapes of the passageways and their connectivity. The images used to generate the composite representation may be recorded preoperatively or intra-operatively during a clinical procedure. In an alternative embodiment, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the patient anatomy. The location can be used to produce both macro-level tracking images of the patient anatomy and virtual internal images of the patient anatomy. Various systems for using fiber optic sensors to register and display an interventional implement together with preoperatively recorded surgical images, such as those from a virtual visualization system, are known. For example U.S. patent application Ser. No. 13/107,562, filed May 13, 2011, disclosing, "Medical System Providing Dynamic Registration of a Model of an Anatomical Structure for Image-Guided Surgery," which is incorporated by reference herein in its entirety, discloses one such system.

The robotic interventional system 100 may further include optional operation and support systems (not shown) such as illumination systems, steering control systems, irrigation systems, and/or suction systems. In alternative embodiments, the robotic system may include more than one robotic assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 2:
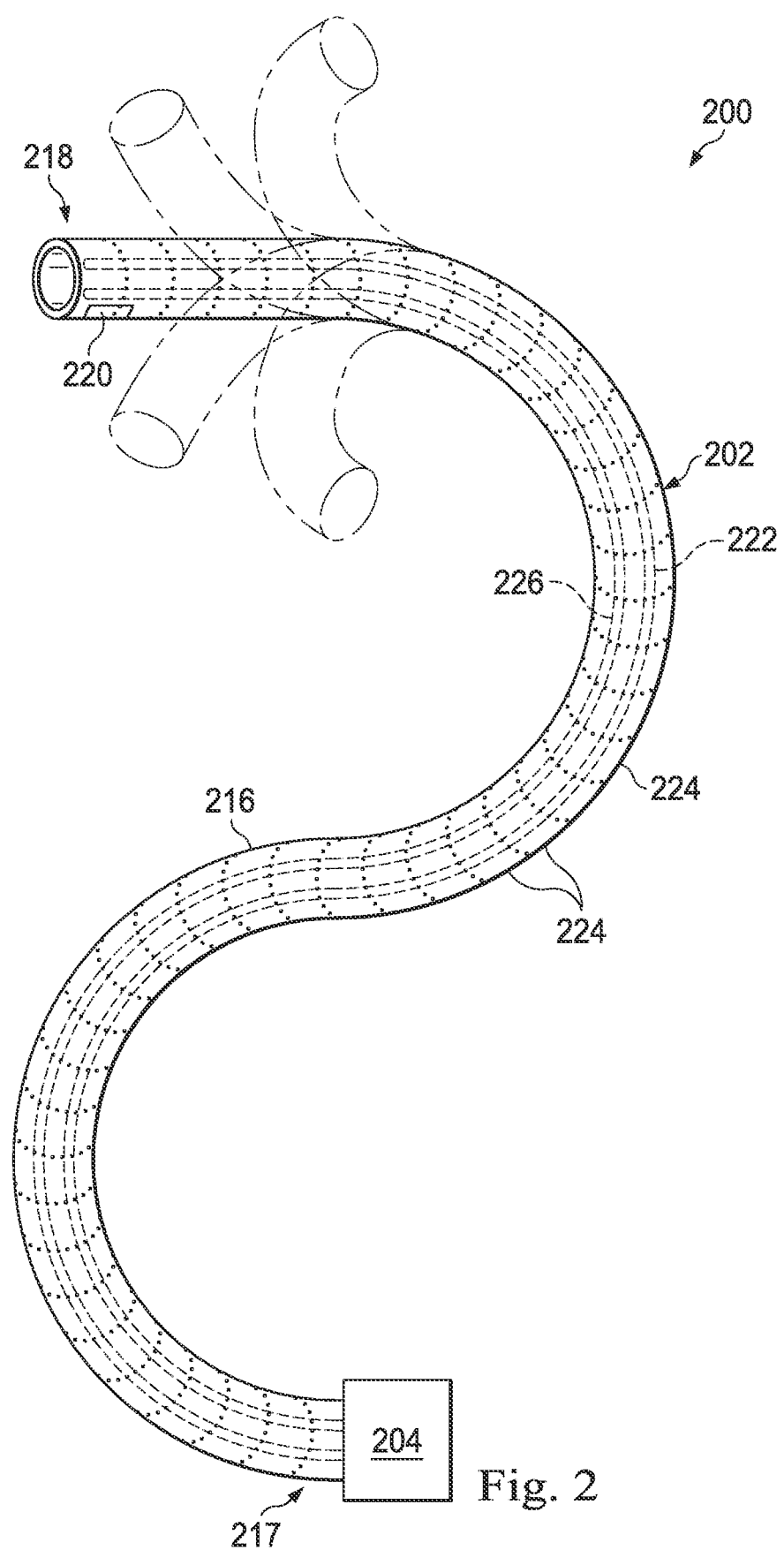
FIG. 2 illustrates an interventional instrument system utilizing aspects of the present disclosure.

FIG. 2 illustrates an interventional instrument system 200 which may be used as the interventional instrument system 104 of robotic interventional system 100. Alternatively, the interventional instrument system 200 may be used for non-robotic exploratory procedures or in procedures involving traditional manually operated interventional instruments, such as endoscopy.

The instrument system 200 includes a catheter system 202 coupled to an instrument body 204. The catheter system 202 includes an elongated flexible catheter body 216 having a proximal end 217 and a distal end or tip portion 218. In one embodiment, the flexible body 216 has an approximately 3 mm outer diameter. Other flexible body outer diameters may be larger or smaller. The catheter system 202 may optionally include a shape sensor 222 for determining the position, orientation, speed, pose, and/or shape of the catheter tip at distal end 218 and/or of one or more segments 224 along the body 216, The entire length of the body 216, between the distal end 218 and the proximal end 217 may be effectively divided into the segments 224. If the instrument system 200 is an interventional instrument system 104 of a robotic interventional system 100, the shape sensor 222 may be a component of the sensor system 108. If the instrument system 200 is manually operated or otherwise used for non-robotic procedures, the shape sensor 222 may be coupled to a tracking system that interrogates the shape sensor and processes the received shape data.

The shape sensor system 222 may include an optical fiber aligned with the flexible catheter body 216 (e.g., provided within an interior channel (not shown) or mounted externally). In one embodiment, the optical fiber has a diameter of approximately 200 µm. In other embodiments, the dimensions may be larger or smaller.

The optical fiber of the shape sensor system 222 forms a fiber optic bend sensor for determining the shape of the catheter system 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389, filed Jul. 13, 2005, disclosing "Fiber optic position and shape sensing device and method relating thereto;" U.S. Provisional Pat. App. No. 60/588,336, filed on Jul. 16, 2004, disclosing "Fiber-optic shape and relative position sensing;" and U.S. Pat. No. 6,389,187, filed on Jun. 17, 1998, disclosing "Optical Fibre Bend Sensor," which are incorporated by reference herein in their entireties. In other alternatives, sensors employing other strain sensing techniques such as Rayleigh scattering, Raman scattering, Brillouin scattering, and Fluorescence scattering may be suitable. In other alternative embodiments, the shape of the catheter may be determined using other techniques. For example, if the history of the catheter's distal tip pose is stored for an interval of time that is smaller than the period for refreshing the navigation display or for alternating motion (e.g., inhalation and exhalation), the pose history can be used to reconstruct the shape of the device over the interval of time. As another example, historical pose, position, or orientation data may be stored for a known point of an instrument along a cycle of alternating motion, such as breathing. This stored data may be used to develop shape information about the catheter. Alternatively, a series of positional sensors, such as EM sensors, positioned along the catheter can be used for shape sensing. Alternatively, a history of data from a positional sensor, such as an EM sensor, on the instrument during a procedure may be used to represent the shape of the instrument, particularly if an anatomical passageway is generally static. Alternatively, a wireless device with position or orientation controlled by an external magnetic field may be used for shape sensing. The history of its position may be used to determine a shape for the navigated passageways.

In this embodiment, the optical fiber may include multiple cores within a single cladding. Each core may be single-mode with sufficient distance and cladding separating the cores such that the light in each core does not interact significantly with the light carried in other cores. In other embodiments, the number of cores may vary or each core may be contained in a separate optical fiber.

In some embodiments, an array of FBG's is provided within each core. Each FBG comprises a series of modulations of the core's refractive index so as to generate a spatial periodicity in the refraction index. The spacing may be chosen so that the partial reflections from each index change add coherently for a narrow band of wavelengths, and therefore reflect only this narrow band of wavelengths while passing through a much broader band. During fabrication of the FBG's, the modulations are spaced by a known distance, thereby causing reflection of a known band of wavelengths. However, when a strain is induced on the fiber core, the spacing of the modulations will change, depending on the amount of strain in the core. Alternatively, backscatter or other optical phenomena that vary with bending of the optical fiber can be used to determine strain within each core.

Thus, to measure strain, light is sent down the fiber, and characteristics of the returning light are measured. For example, FBG's produce a reflected wavelength that is a function of the strain on the fiber and its temperature. This FBG technology is commercially available from a variety of sources, such as Smart Fibres Ltd, of Bracknell, England. Use of FBG technology in position sensors for robotic surgery is described in U.S. Pat. No. 7,930,065, filed Jul. 20, 2006, disclosing "Robotic Surgery System Including Position Sensors Using Fiber Bragg Gratings," which is incorporated by reference herein in its entirety.

When applied to a multicore fiber, bending of the optical fiber induces strain on the cores that can be measured by monitoring the wavelength shifts in each core. By having two or more cores disposed off-axis in the fiber, bending of the fiber induces different strains on each of the cores. These strains are a function of the local degree of bending of the fiber. For example, regions of the cores containing FBG's, if located at points where the fiber is bent, can thereby be used to determine the amount of bending at those points. These data, combined with the known spacings of the FBG regions, can be used to reconstruct the shape of the fiber, Such a system has been described by Luna Innovations, Inc. of Blacksburg, Va.

As described, the optical fiber may be used to monitor the shape of at least a portion of the catheter system 202. More specifically, light passing through the optical fiber is processed to detect the shape of the catheter system 202 and for utilizing that information to assist in surgical procedures. The sensor system (e.g. sensor system 108) may include an interrogation system for generating and detecting the light used for determining the shape of the catheter system 202. This information, in turn, can be used to determine other related variables, such as velocity and acceleration of the parts of an interventional instrument. The sensing may be limited only to the degrees of freedom that are actuated by the robotic system, or may be applied to both passive (e.g., unactuated bending of the rigid members between joints) and active (e.g., actuated movement of the instrument) degrees of freedom.

The interventional instrument system may optionally include a position sensor system 220. The position sensor system 220 may be a component of an electromagnetic (EM) sensor system with the sensor 220 including one or more conductive coils that may be subjected to an externally generated electromagnetic field. Each coil of the EM sensor system 220 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of an EM sensor system is provided in U.S. Pat. No. 6,380,732, filed Aug. 11, 1999, disclosing "Six-Degree of Freedom Tracking System Having a Passive Transponder on the Object Being Tracked," which is incorporated by reference herein in its entirety.

The flexible catheter body 216 includes a channel sized and shaped to receive an auxiliary tool 226. Auxiliary tools may include, for example, image capture probes, biopsy devices, laser ablation fibers, or other surgical, diagnostic, or therapeutic tools. Auxiliary tools may include end effectors having a single working member such as a scalpel, a blade, an optical fiber, or an electrode. Other end effectors may include a pair or plurality of working members such as forceps, graspers, scissors, or clip appliers, for example. Examples of electrically activated end effectors include electrosurgical electrodes, transducers, sensors, and the like. In various embodiments, the auxiliary tool 226 may be an image capture probe including a distal portion with a stereoscopic or monoscopic camera disposed near the distal end 218 of the flexible catheter body 216 for capturing images (including video images) that are processed for display. The image capture probe may include a cable coupled to the camera for transmitting the captured image data. Alternatively, the image capture instrument may be a fiber-optic bundle, such as a fiberscope, that couples to the imaging system. The image capture instrument may be single or multi-spectral, for example capturing image data in the visible spectrum, or capturing image data in the visible and infrared or ultraviolet spectrums.

The flexible catheter body 216 may also house cables, linkages, or other steering controls (not shown) that extend between the instrument body 204 and the distal end 218 to controllably bend or turn the distal end 218 as shown for example by the dotted line versions of the distal end. In embodiments in which the instrument system 200 is actuated by a robotic assembly, the instrument body 204 may include drive inputs that couple to motorized drive elements of the robotic assembly. In embodiments in which the instrument system 200 is manually operated, the instrument body 204 may include gripping features, manual actuators, and other components for manually controlling the motion of the instrument system. The catheter system may be steerable or, alternatively, may be non-steerable with no integrated mechanism for operator control of the instrument bending. Also or alternatively, the flexible body 216 can define one or more lumens through which interventional instruments can be deployed and used at a target surgical location.

In various embodiments, the interventional instrument system 200 may include a flexible bronchial instrument, such as a bronchoscope or bronchial catheter for use in examination, diagnosis, biopsy, or treatment of a lung. The system is also suited for navigation and treatment of other tissues, via natural or surgically created connected passageways, in any of a variety of anatomical systems including the colon, the intestines, the kidneys, the brain, the heart, the circulatory system, or the like.

While an instrument (e.g. catheter 202) is navigated through anatomic passageways, the clinician may view an endoscopic camera image and a virtual anatomical image generated from preoperative or intraoperative imaging. The camera image and the virtual image are registered to provide the clinician with an intuitive navigation experience. If an endoscopic camera is not used, for example because the anatomic passageway is not sized to accommodate a camera, registration of the distal end of the catheter with the virtual anatomical image is needed because the clinician may rely on the virtual anatomical image to provide navigation guidance and pose confidence when performing a procedure such as a biopsy. With regions of the patient anatomy that are dynamic in normal function (e.g., heart, lungs, kidneys, liver, blood vessels), substantially continuous dynamic registration of the instrument and the virtual anatomical image is needed. As will be described, a shape sensor located within the catheter may be used to both model cyclic anatomical motion and track the movement of the instrument within the moving anatomy.

FIG. 3a illustrates a general method 300 for modeling cyclic anatomical motion according to an embodiment of this disclosure, One or more of the processes 302-308 of the method 300 may be implemented, at least in part, in the form of executable code stored on non-transient, tangible, machine-readable media that when run by one or more processors may cause the one or more processors to perform one or more of the processes 302-308. At 302, a shape sensor, such as an optical fiber shape sensor, extends within an interventional instrument (e.g. catheter 202). The interventional instrument is inserted into a dynamic anatomical passageway of a patient and fixed with respect to the anatomical passageway. For example, the instrument may be wedged into a tight passageway and held in place by a frictional force. Alternatively, the instrument may be fixed using retractable anchors, inflatable fixation devices or other anchoring mechanisms known in the art. The instrument is constrained within the passageway but compliantly moves with the passageways during the anatomic motion cycle. The shape sensor of the interventional instrument is interrogated and returns strain data used to determine a composite shape of the optical fiber, including reconstructing the bending, twisting, compression, and other shape characteristics that define the overall composite shape of the optical fiber. From this shape information, the pose of a discrete point P, such as a distal end or other point along the instrument, may be filtered and determined. The shape sensor is interrogated at a plurality of times during a patient anatomical motion cycle, and the pose of the point P may be determined at each time interval. For convenience and without limitation, this disclosure will describe the use of systems and methods with reference to the respiration cycle as the anatomical motion cycle. It is understood that the same systems and methods are applicable to other forms of cyclic or otherwise predictable anatomic motion such as cardiac motion.

At 304, a set of three dimensional pose differentials is determined for the point P with respect to at least one reference element R (See, FIG. 6) at each of the plurality of time intervals. In other words, the difference between the reference element R and the point P is determined at each dine interval within the anatomic motion cycle. The difference may be based upon the position, such as using a position difference vector between P and R. Additionally or alternatively, the difference may be based upon orientation. Any partial pose combination of position and orientation differences may be used to determine differentials between element R and point P. Each three-dimensional pose differential in the set may be expressed, for example, as a three dimensional vector between reference element R and the point P. The reference element R may include a localization marker cable of being sensed by the previously described position sensor system (e.g., an EM sensor system). Thus, the reference element R may include electromagnetic coils or alternatively may include infrared light emitting diodes, reflective markers, or other elements used to determine the location of the reference element. The reference element R may be positioned on the surface of the patient anatomy or internal to the patient anatomy at a location that experiences little or no movement due to the cyclical anatomical motion or to a stationary fixture external to the patient anatomy. Alternatively, the reference element R may be positioned at a location that experiences cyclical anatomical motion with a discernible periodic difference between the motion of the element R and the motion of the point P. Suitable locations for positioning the reference element R may include, for example, the sternum, the main carina (i.e., the bottom of the trachea where the trachea divides into the left and right main bronchus leading to the lungs), a location on a vertebral body of the patient's spine, or any other anatomical location that experiences movement with a periodic difference from the movement of the point P.

At 306, a periodic signal related to the anatomical motion cycle is determined from the set of three dimensional pose differentials. For example, where the set of three-dimensional pose differentials is expressed as a set of three-dimensional vectors between reference element R and the point P, a periodic signal with well-defined phases or stages corresponding to distinct states of anatomical motion is extracted from the set of three-dimensional vectors. For example, in one embodiment, the length of each vector is measured, and a maximum state pose differential (e.g., longest vector) and a minimum state pose differential (e.g., shortest vector) are identified for the point P. The maximum state pose differential is the maximum three-dimensional difference in position and orientation between the point P and the reference element R. The minimum state pose differential is the minimum three-dimensional difference in the position and orientation between the point P and the reference element R. If, for example the anatomical motion is respiration, the maximum state pose differential is associated with the pose of point P at the distinct anatomical state of full inspiration and the minimum state pose differential is associated with the pose of point P at the distinct anatomical state of full expiration. The intermediate state pose differentials correspond to intermediate stages of inhalation and exhalation. From these maximum, minimum, and intermediate states, a distinct periodic signal can be extracted. In another embodiment, a particular aspect of the set of three-dimensional vectors between the reference element R and the point P may be used to extract a periodic signal. For example, the periodic signal may be extracted based upon a single dimension (e.g., the x, y, or z-coordinate) differential. Alternatively, the periodic signal may be extracted based upon a differential in the angle of the vector. Alternatively, the periodic signal may be extracted based upon a change rate of displacement for the point P with respect to the reference element R. For example, as one or more coordinates of the three-dimensional vector between the point P and the reference element R changes signs (e.g., positive to negative), maximum and minimum values for the periodic signal may be extracted. Alternatively, the periodic signal may be extracted, based at least in part upon, a mechanism (e.g., a respirator) that is causing the anatomic motion or from a mechanism (e.g., an external respiration monitor) that is monitoring the anatomic motion.

At 308, first and second time parameters, from the plurality of time parameters, corresponding to first and second anatomic states, respectively, are identified and stored. For example, the first anatomic state may be full inspiration and the second anatomic state may be full expiration. The use of two time parameters to correspond to two anatomic states is illustrative and not intended to be limiting. Alternatively, a single or three or more time parameters from the plurality of time parameters may correspond to a single or to three or more anatomic states, respectively. The first and second time parameters may also be normalized such that parameters $t_{1st}=1$ and $t_{2nd}=0$. These maximum and minimum time parameters may be used, for example, to model the motion cycle for an intermediate time parameter $t_x$ where $t_{1st}=1, \ldots, t_x, \ldots, t_{2nd}=0$. (See, FIG. 6) In the embodiment of FIG. 6, the displacements recorded at those first and second time parameters are considered the maximum pose for point P ($P_{1st}$) in the motion cycle and the minimum pose for point P ($P_{t-2nd}$) in the motion cycle, respectively. The first pose for point $P_{t-1st}$ and the second pose for point P ($P_{t-2nd}$) may also be stored. The process 300 may be repeated for different points on the shape sensor or when the tool has been moved to a new area of interest.

FIG. 3b illustrates a general method 310 for modeling cyclic anatomical motion according to another embodiment of this disclosure. One or more of the processes 312-314 of the method 310 may be implemented, at least in part, in the form of executable code stored on non-transient, tangible, machine-readable media that when run by one or more processors may cause the one or more processors to perform one or more of the processes 312-314. At a process 312, a shape sensor, such as an optical fiber shape sensor, extends within an interventional instrument (e.g. catheter 202). The interventional instrument is inserted into a dynamic anatomical passageway of a patient and fixed with respect to the anatomical passageway as described above for process 302. The shape sensor of the interventional instrument is interrogated and returns strain data used to determine a composite shape of the optical fiber, including reconstructing the bending, twisting, compression, and other shape characteristics that define the overall composite shape of the optical fiber. From this shape information, the pose of a discrete point $P_1$, such as a distal end or other point along the instrument, may be filtered and determined. The shape sensor is interrogated at a plurality of times during a patient anatomical motion cycle, and the pose of the point $P_1$ may be determined at each time interval. Likewise, the shape sensor may be interrogated at multiple discrete points $P_1$-$P_n$ along the instrument during the anatomical motion cycle to determine the pose of a set of points at each time interval.

In alternative embodiments, a shape sensor used for tracking respiration phase cycle may be mounted to the patient's chest rather than located inside of the patient's lungs. Alternatively, because a respiration phase cycle may be determined from the frequency of a signal without regard to absolute position, the frequency content of velocity and acceleration signals may also be used to determine respiration phase cycle, Accelerometers and gyroscopes, including wireless versions, used to track velocity and/or acceleration may be used as sensors to determine the respiration phase cycle.

A shape sensor or any other type of sensor used to track respiration may be actuated in any of a variety of ways. For example, the sensor may begin and/or end tracking in response to a user command such as activation of a trigger deployable based upon motion of the user's hand or foot, a verbal command, an eye gaze command, or use of user controlled implement such as a mouse. Sensors may also be actuated when actuation commands to the medical instrument have terminated. For example, when the medical instrument reaches a target location prior to a biopsy procedure, the sensor to track respiration may be activated. Alternatively, sensors may be actuated when the user commanded position is constant (e.g., when the user input control is maintained in a constant position)

At 314, a periodic signal related to the anatomical motion cycle is determined. In one embodiment, the anatomical motion cycle may be a respiratory phase cycle. The respiratory phase cycle may be tracked as described above at process 306. Other techniques for tracking the respiratory phase cycle may also be suitable. For any of the described techniques, the extreme phases of respiration may be differentiated by the fact that a typical human respiration cycle lingers in the expiration phase longer than it does in the inspiration phase.

In one example of respiration phase cycle tracking, the main carina of the patient anatomy may serve as the reference element R because this reference element experiences relatively little movement during respiration as compared to more peripheral areas of the lung that experience greater displacement during inhalation and exhalation. A set of three dimensional pose differentials is determined for each point $P_1$-$P_n$ with respect to at least one reference element R (See, FIG. 6) at each of the plurality of time intervals. In other words, the difference between the reference element R and the points $P_1$-$P_n$ is determined at each time interval within the anatomic motion cycle. From the maximum, minimum, and intermediate differential states associated with these points $P_1$-$P_n$, a distinct periodic signal can be extracted.

Alternatively, various data mapping tools such as look-up tables may be used for respiratory phase cycle tracking based on the location of a point P (e.g., the location of the point at the distal tip of the catheter) within the lung. For example, as shown at FIG. 7, a look-up table 600 provides a listing of locations 602 within the anatomy. In a human lung, for example, the locations may be associated with lobes of the lung (e.g., right middle lobe, left superior lobe) and/or with respect to distance from the main carina (e.g., primary bronchi, secondary bronchi, tertiary bronchi, bronchioles). For each location in the lung, a particular type of preferred motion measurement 604 may be applied. For example, a Motion Measurement A for tracking a direction of motion (e.g., a direction perpendicular to the direction of the airway) may be associated with a Location 1 (e.g., a tertiary bronchi in the left inferior lobe). As another example, the preferred motion measurement, Motion Measurement A, may be based upon the expected primary direction of expansion of the lungs. The preferred motion measurement for the lower (inferior) right lung could be along a generally left-right axis. The preferred motion measurement for the middle right lung could be along a generally superior-inferior axis (i.e., axis extending generally in a head-to-toe-direction), From the maximum, minimum, and intermediate differential states associated with a point P at a particular location 602, a distinct periodic signal can be extracted.

As another example, a look-up table 610 provides a listing of locations 612 within, for example, the lung. For each location in the lung, a different set of points along the shape sensor may be tracked to return a most accurate motion signal. For example, a Set A of shape sensor points (e.g., points clustered near the distal end of the catheter) may be associated with a Location 1 (e.g., a tertiary bronchi in the left inferior lobe). As another example, if location in the listing of locations 612 is close to the pleura or close to rigid body structures (e.g., cartilage or bone), the expected lung movement may be small. In this example, if a distal end of an instrument is located close to the pleura or rigid body structures, a preferred set of shape sensor points may be located along a more proximal length of the instrument, away from the distal end. As another example, if a location in the listing of locations 612 is in an anatomic area that experiences rotational motion instead of translational motion, the set of shape sensor points to be tracked may be located in the area of the anatomy receiving rotational motion. From the maximum, minimum, and intermediate differential states associated with the set of points at a particular location 612, a distinct periodic signal can be extracted.

Alternatively, parallel sensors may be used to track the respiration phase cycle. For example, vision-based sensor data from a vision-based sensor (e.g. an endoscope) positioned within the lungs that moves with the lungs during respiration is compared to EM sensor data from an EM sensor positioned at a relatively stationary location such that the airway moves relative to the EM sensor. The difference between the tracked data from these sensors may be used to extract a distinct periodic signal for the respiration phase cycle.

Alternatively, the respiration phase cycle may be tracked by taking a relatively noisy set of data from the shape sensor and/or other sensors and extracting cardiac and respiration phase cycles. More specifically, a cardiac frequency (e.g., number of heart beats per minute) and a respiration frequency (e.g., number of exhalations per minute) may be computed from the set of sensor data without regard to the phase (or stage of the cycle) for each cyclic motion. The estimated cardiac and respiration frequencies may be used to digitally filter the sensor data at one or more time intervals to extract phase information.

Although respiration phase cycle tracking may be performed by tracking shape sensor or other sensor signals as described above, other techniques for tracking the respiratory phase cycle may also be suitable. For example, a respiration phase cycle may be determined by applying a bandpass filter to the measured data (e.g., position data, velocity data, shape data) near the expected frequency of respiration (e.g., exhalations/minute) and extracting the respiration phase cycle from the filtered data. The bandpass filter may select only frequencies between a predefined maximum and minimum frequency near the expected frequency of respiration.

In another example, respiration phase cycle may be determined by comparing commanded instrument motion to sensed instrument motion. In a teleoperational surgical system, known motion commands are provided to move the teleoperationally controlled instrument. For example, known commands are provided to motor actuators that control the steerable distal end of an instrument. The actual movement may be determined from the shape sensor or other sensor data. The actual movement, as determined from the sensor data, may be subtracted from the commanded motion to isolate the remaining motion due to anatomical motion such as respiration.

Figure 5:
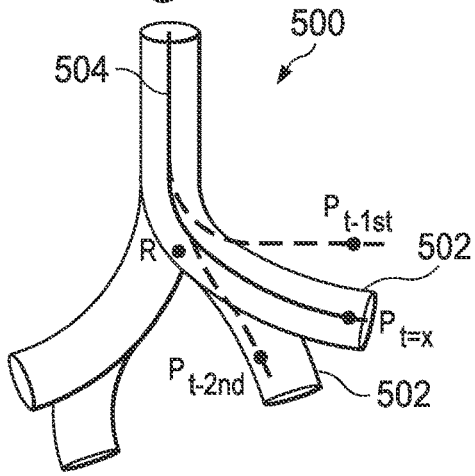
FIG. 5 illustrates maximum and minimum state pose differentials for a point P of an interventional instrument during cyclic anatomical motion.

FIG. 5 provides a three dimensional image 500 of cyclically moving anatomical passageways 502 in which an interventional instrument 504 extends. The pose of the instrument 504 is measured at point P for a plurality of time intervals during the cyclic anatomical motion, and the pose is compared to the reference element R for each of the time intervals. The maximum pose differential occurs at and the minimum pose differential occurs at $P_{t-2nd}$.

Figure 4:
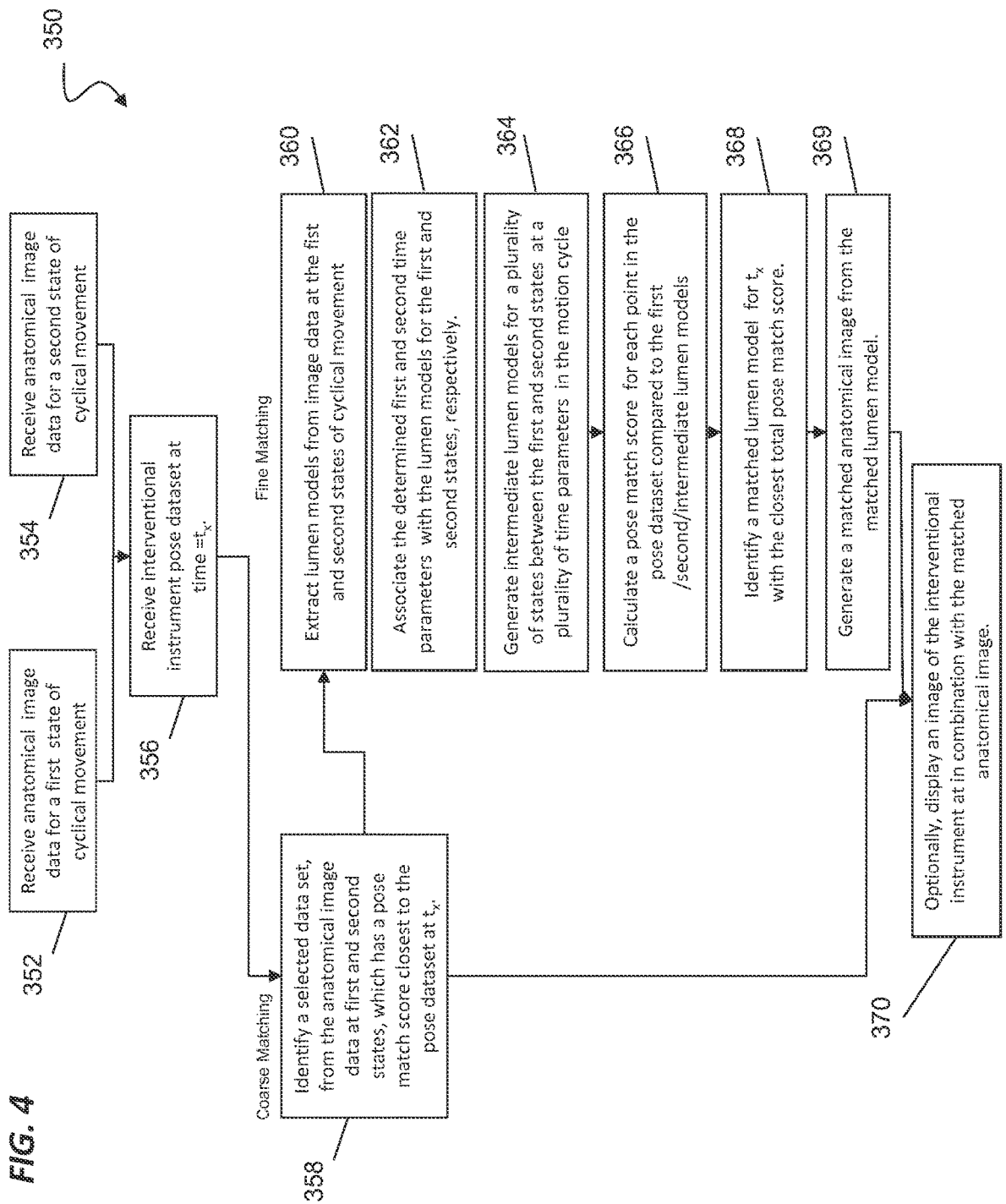
FIG. 4 illustrates a method of tracking an interventional instrument within a patient anatomy during cyclic anatomical motion.

FIG. 4 illustrates a method 350 of tracking an interventional instrument (e.g. catheter 202) within a patient anatomy during cyclic anatomical motion after modeling the cyclical anatomical motion using method 300, 310 or another suitable method. One or more of the processes 352-370 of the method 350 may be implemented, at least in part, in the form of executable code stored on non-transient, tangible, machine-readable media that when run by one or more processors may cause the one or more processors to perform one or more of the processes 352-370. At 352, anatomical image data from a preoperative or intraoperative anatomical image for first state of cyclical movement is received for processing. For example, if the anatomic cycle is respiration, a patient may be imaged at full inspiration, the state that corresponds to the first or maximum state of the cyclical movement. At 354, anatomical image data from a preoperative or intraoperative anatomical image for a second state of cyclical movement is received for processing. For example, a patient may be imaged at full expiration, the state that corresponds to the second or minimum state of the cyclical movement. In alternative embodiments, the first and second states of cyclical motion need not correspond to maximum or minimum extrema, but may correspond to other identified stages of the cycle. In still other alternative embodiments, image data from a single state of cyclical motion or more than two states of the cyclical motion may be matched to the extracted periodic signal.

At 356, during the interventional procedure, the shape sensor of the interventional instrument is interrogated at a time interval $t=t_x$, and a pose dataset for a plurality of points along the shape sensor at $t=t_x$ is collected. To register the interventional instrument with a preoperative or intraoperative image at $t=t_x$, a coarse matching procedure, optionally supplemented by a fine matching procedure, may be used.

To perform a coarse matching, at 358 a three-dimensional difference between the pose dataset of the plurality of points along the shape sensor at $t_x$ and the anatomical image data at the first state of cyclical motion is calculated to determine a pose match score for the first state. Additionally, a three dimensional difference between the pose dataset of the plurality of points along the shape sensor at $t_x$ and the anatomical image data at the second state of cyclical motion is calculated to determine a pose match score for the second state. The pose match scores for the first and second states indicate which state has anatomical image data most similar to the shape sensor at $t_x$. The state with the best pose match score, i.e. the state that most closely matches the shape sensor, is identified as the matching anatomical image data set. The best pose match score may be based, for example, upon one or more of a comparison of distance, orientation, shape matches, or navigation decision history.

Optionally, at 370, a virtual image of the interventional instrument is displayed in combination with the matched anatomical image. For example, the image of the interventional instrument may be gated and displayed with the matched anatomical image from either the first or second state. The displayed instrument shape may be modified to align with the matched anatomical image. Alternatively, the image may be modified to fit with the measured shape. Also optionally, the matched anatomical image may be presented simultaneous (e.g., in a different window of a display or on a different display) with a current endoscopic image from the interventional instrument.

Figure 6:
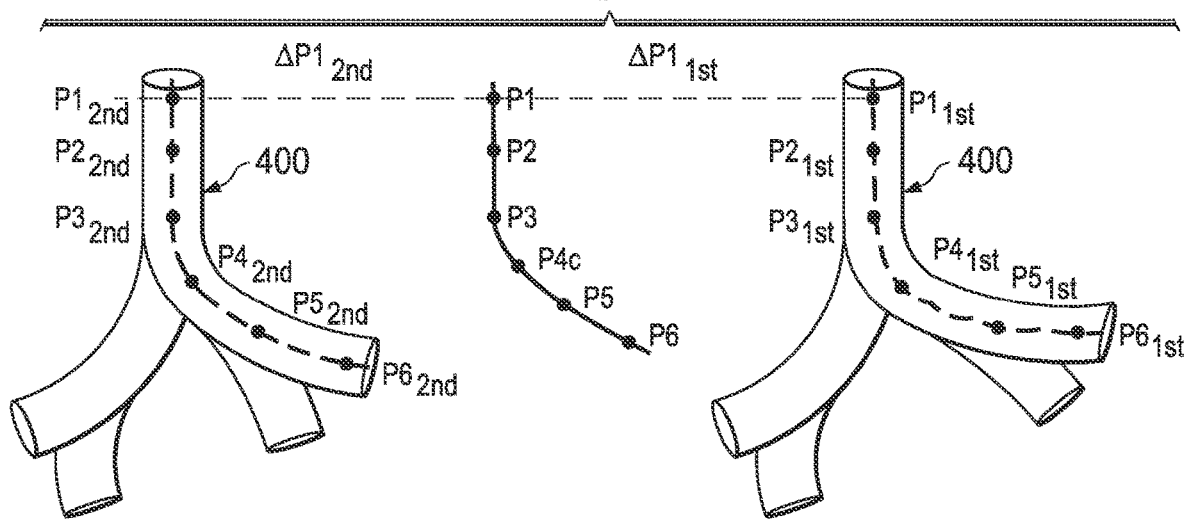
FIG. 6 illustrates an intervention instrument pose dataset compared to the anatomical image data at maximum and minimum states according to an embodiment of the present disclosure.

FIG. 6 illustrates an interventional instrument pose dataset P1-P6 compared to the anatomical image data at first state $P1_{1st}$-$P6_{1st}$ and second state $P1_{2nd}$-$P6_{2nd}$ for generating a pose match score. The points $P1_{1st}$-$P6_{1st}$ may follow, for example, a centerline through the lumen of the anatomic passageway 400 in the state of full inhalation. The points $P1_{2nd}$-$P6_{2nd}$ may follow, for example, a centerline through the lumen of the anatomic passageway 400 in the state of full exhalation. A three dimensional difference $\Delta P1_{1st}$ is determined between the instrument point P1 and the point $P1_{1st}$ from the anatomic image data from the state of full inhalation. A three dimensional difference is further computed for each instrument point and a corresponding point from the anatomic image at full inhalation. The instrument insertion length may be used, when the instrument is moving, to approximate the association between the instrument points P1-P6 and the anatomic image points $P1_{1st}$-$P6_{1st}$. Instrument and image points can be associated using best-fit techniques. For example, for a given instrument point, the closest image point that is within an anatomic passageway may be chosen. The instrument insertion length may be used to limit the choice to points in the image that are approximately the insertion length away from the insertion point. The three-dimensional differences at each point are combined (e.g., added or averaged) to generate the pose match score for the first state. Likewise, a three dimensional difference $\Delta P1_{2nd}$ is determined between the instrument point P1 and the point $P1_{2nd}$ from the anatomic image data from the state of full exhalation. A three dimensional difference is further computed for each instrument point and a corresponding point from the anatomic image at full exhalation. The three-dimensional differences at each point are combined (e.g., added or averaged) to generate the pose match score for the second state.

To enable continuous tracking and dynamic registration of the interventional instrument with the endoscopic image and/or the virtual anatomical image and to avoid the jerky display associated with the coarse matching and gating techniques, a fine matching procedure may be performed. Referring again to FIG. 4, to perform fine matching, at 360 lumen models are extracted from the image data at the first and second states of cyclical movement. The lumen model may be any form of anatomic representation including, for example, a centerline model, an image-voxel model, a geometric (e.g., mesh) model, or a parametric model. On example of a method of modeling a branching anatomy is provided in U.S. patent application Ser. No. 13/893,040 and 13/892,871 filed May 13, 2013, disclosing "Systems and Methods for Registration of a Medical Device Using a Reduced Search Space," which is incorporated by reference herein in its entirety, Another example of a method of modeling a branching anatomy using a mesh deformation technique is provided in U.S. Provisional Pat App. No. 61/935,547 filed Feb. 4, 2014, disclosing "Systems and Methods for Non-rigid Deformation of Tissue for Virtual Navigation of Interventional Tools," which is incorporated by reference herein in its entirety.

At 362, the determined first and second time parameters $t_{1st}=1$, $t_{2nd}=0$) from process 308 are associated with the respective first state and second state lumen models. The first and second time parameters are determined from, for example, the modeled anatomic motion as described in method 300 or other cyclic motion modeling techniques. At 364, a plurality of intermediate lumen models are created by interpolating intermediate movement states between the first and second states for a plurality of time parameters $(t_{1st}=1, \ldots, t_x, \ldots, t_{2nd}=0)$ in the modeled motion cycle.

At 366, a pose match score is calculated for each intermediate lumen model by performing a three dimensional comparison between the interventional instrument pose dataset P1-P6 and corresponding points on each intermediate lumen model. A pose match score is also calculated for the lumen models at the maximum and minimum states. At 368, the lumen model with the best pose match score, i.e. the lumen model that most closely matches the shape of the shape sensor, is identified as the matched lumen model. At 369, a matched anatomical image data set is generated from the matched lumen model. Generating the matched anatomical image data set may include applying a deformation vector field. The use of a deformation vector field to generate image data is described in greater detail in U.S. patent application Ser. No. 61/935,547, which is incorporated by reference herein in its entirety. At 370, optionally, a virtual image of the interventional instrument in the shape at $t_x$ is displayed in combination with the matched anatomical image data. Also optionally, the matched anatomical image may be presented simultaneous (e.g., in a different window of a display or on a different display) with a current endoscopic image from the interventional instrument.

Figure 9:
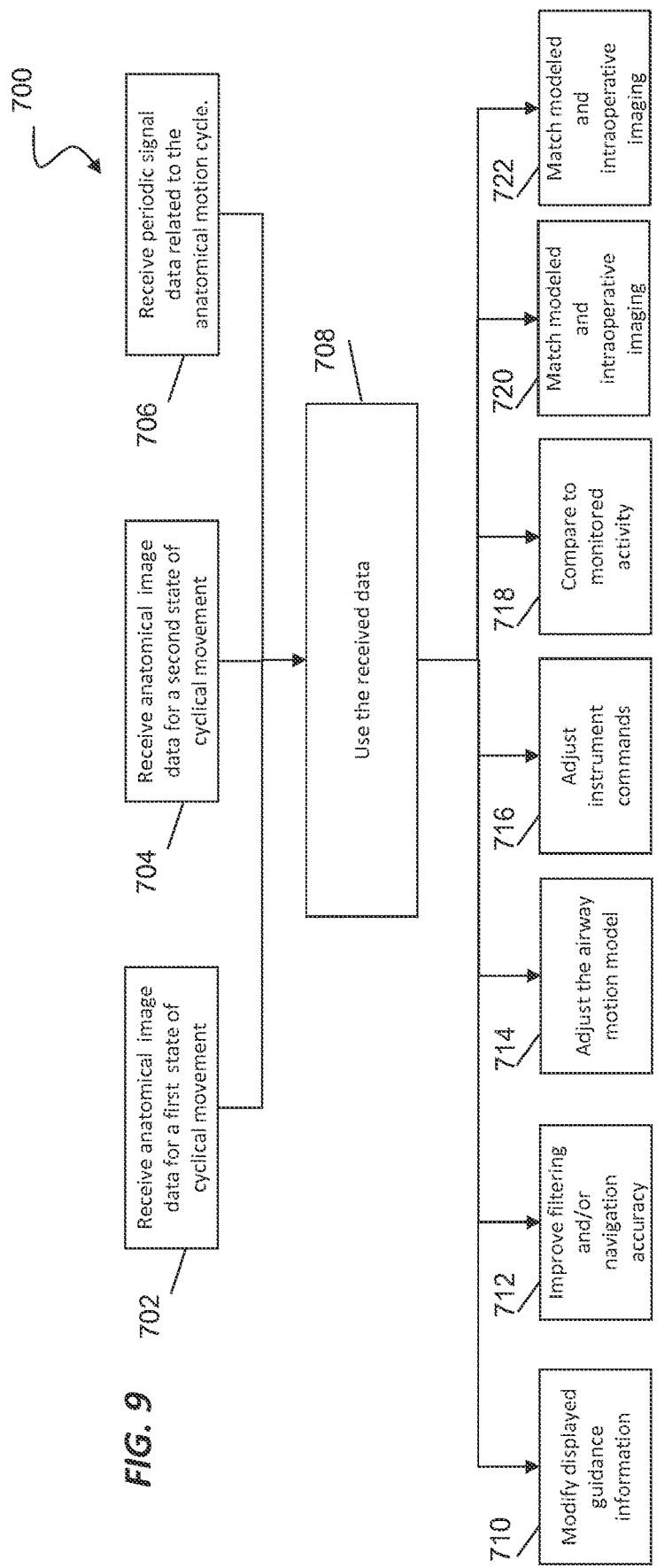
FIG. 9 illustrates a method of using periodic signal data related to an anatomical motion cycle.

FIG. 9 illustrates a method 700 of using the periodic signal data from a method 300 or 310 to improve an interventional procedure using an interventional instrument (e.g. catheter 202) within a patient anatomy. One or more of the alternative processes 702-722 of the method 700 may be implemented, at least in part, in the form of executable code stored on non-transient, tangible, machine-readable media that when run by one or more processors may cause the one or more processors to perform one or more of the processes 702-722. Optionally, at a process 702 anatomical image data from a preoperative or intraoperative anatomical image for first state of cyclical movement is received for processing. For example, if the anatomic cycle is respiration, a patient may be imaged at full inspiration, the state that corresponds to the first or maximum state of the cyclical movement. Optionally, at a process 704 anatomical image data from a preoperative or intraoperative anatomical image for a second state of cyclical movement is received for processing. At a process 706, periodic signal data related to an anatomical motion cycle (e.g., the periodic signal related to the respiratory phase cycle as determined in methods 300 or 310) is received. At a process 708, the received image and signal data may be processed by a control system (e.g. control system 112) to improve aspects of planning, navigation, and instrument command during an interventional procedure.

Optionally, at a process 710, the guidance information displayed to a clinician on a display (e.g., display 110) is modified using the respiratory phase cycle data. For example, the location of a target anatomical structure (such as a tumor to be biopsied) may be adjusted in the displayed image based upon the current stage of the respiratory phase cycle. Adjusting the displayed image may include interpolating the image data from the first and/or second state of cyclical movement to the current stage of the respiratory phase cycle. The guidance information may also be modified by deforming the images, anatomic model, or other anatomic representation based on a best match image or on an interpolated representation, for example as described in method 350.

Another technique for modifying displayed guidance information is stabilizing a camera view (e.g. an endoscope view) to give the appearance of a stationary anatomy to the clinician viewing the display. For example, the operation of the camera may be synchronized with the respiratory phase cycle data so that a zoom operation is timed to the respiration. The zoom effect may be accomplished, for example, by physically moving the camera along the axis of the anatomic passageway, by operating a digital zoom feature of the camera or an image processor, or by operating an optical zoom feature of the camera.

Another technique for modifying the displayed guidance information is displaying an indicia of uncertainty together with the image of the anatomy (e.g. single image, model, other anatomic representation) and the interventional instrument in the sensed position and/or shape. The anatomic representation may be a matched image/model from the first or second state of anatomic motion or may be an interpolated image/model. The indicia of uncertainty may be the clarity of the instrument image, such as a blurry image that varies as the phase of respiration varies from the phase at which image was acquired. Other indicia of uncertainty include a graphical bubble, color indicator, or alphanumeric indicator that vary as the phase of respiration varies from the phase of respiration at which the image of the anatomy was acquired.

At a process 712, improved filtering and/or navigation accuracy may be achieved using the respiratory phase cycle data. For example, the matched or interpolated airway model, (generated as previously described) may be used, together with the measured shape of the interventional instrument to predict the airway in which the distal end of the interventional instrument is positioned. This prediction may be based upon which airway in the matched or interpolated airway model best fits the shape of the interventional instrument. In another example, the respiratory phase information may be used to perform the transformation (e.g., translation, rotation, and sizing) of the anatomic model to a patient frame of reference. Transformation methods such as iterative closest point (ICP)-based algorithms, vision-based tracking, or external optical-based tracking may adjusted by removing the open-loop respiratory motion, as described by the respiratory phase cycle data, from the sensor data used to estimate the transformation.

Another technique for improving temporal filtering and reducing lag time involves filtering the data from the EM coil sensors based upon the known respiration phase. For example, the estimated respiration motion model may be used to anticipate when the EM sensor data will register a quick movement (e.g. a quick motion associated with sharp inhalation). During this quick motion phase of the respiration cycle, the sensor data may be filtered based upon (including averaged or compared to) an expected signal or sensor measurement.

Another technique for improved sensor data filtering includes using the respiratory and/or cardiac phase cycle data to filter respiration-based motion and cardiac-based motion from the measured shape sensor signal. With the anatomic motion removed from the sensor signal, the displayed shape of the interventional instrument may be stabilized.

Another technique for improving navigation includes using the respiratory phase cycle data to assist in lumen navigation selection. Decisions regarding the next lumen to which the medical instrument should be navigated generally have a higher level of confidence when determined at the same phase of respiration as the phase at which the image was captured. Without respiratory phase cycle data, lumen selection navigation decisions made at time instances between the phases at which the images were captured have a lower level of confidence. Because the respiratory phase cycle data provides information about the location of the moving lumens at various times during the respiration cycle, lumen selection navigation decisions may be made with greater confidence.

At a process 714, the respiratory phase cycle data may be used to adjust the airway motion model. For example, a single recorded patient-specific image (e.g., a CT image) may be animated or modified based upon a generic (e.g., non-patient specific) anatomic model or anatomic atlas (e.g., a two- or three-dimensional view of the airway tree) for the measured stage of the respiratory phase cycle. Another technique for adjusting the airway motion model uses the respiratory phase cycle data to scale the amplitude of the displayed or used deformation, More specifically, if a patient's normal breathing pattern does not extend all the way to full inhalation and/or full exhalation (the extremes as originally imaged), the actual measured deformation, as determined from the respiratory phase cycle data, is used to adjust the displayed motion of the anatomic model to the patient's normal breathing pattern.

At a process 716, the commands issued by the user, via the control system, to the motors actuating the medical instrument may be adjusted based upon the respiratory phase cycle data. For example, a periodic offset may be added to the command signals to move the distal tip of the interventional instrument with the movement of the anatomy. The periodic offset may be determined from the respiratory phase cycle data to minimize or eliminate the relative movement of the distal tip of the interventional instrument relative to the anatomy.

Another technique for adjusting the instrument commands includes providing the user with a timing indicator which identifies to the user the optimal time(s) to command movement of the interventional instrument. For example, based upon the respiratory phase cycle data, a timing indicator may be provided when the airways experience the least amount of movement so that a clinician may intubate a patient at the time in the respiratory cycle when the risk of injury, due to anatomic movement, is lowest. Alternatively, the control system 112 may prevent commanded motion of the instrument at stages of greatest movement. Alternatively, control system 112 may delay the commanded motion until a stage of minimal respiratory movement is reached, as predicted by the respiratory phase cycle data. Alternatively, the trajectory of the commanded motion may be synchronized with the anatomic motion cycle.

Another technique for adjusting, the instrument commands includes adjusting a commanded position or orientation of the interventional instrument to minimize the amount of bending in an auxiliary tool (e.g. a biopsy needle) that extends from the catheter. More specifically the commanded approach angle or approach position for the needle may be modified to minimize the degree to which the needle pivots about or bends as it passes through the airway wall.

At a process 718, the actual respiration motion (including particular phases of the motion such as the actual inspiration and expiration extrema) may be monitored and compared to the motion expected based upon the respiratory phase cycle data. If a predefined difference between the expected motion and the actual motion is measured, the clinician may be provided with a visual, audible, or tactile alert of a potentially dangerous situation. Alternatively, if a predefined difference between the expected motion and the actual motion is measured, the respiratory phase cycle data and the resulting expected motion model may be adjusted for the particular region of the lung in which the instrument is located. The adjustment may occur responsive to a user command allowing the adjustment or may be made without user input.

At a process 720, the respiratory phase cycle data may be used to match modeled and intraoperative images or models. For example, the anatomic model (e.g. a CT-based model) at a particular stage of respiration may be matched and displayed with the intraoperative camera image (e.g. the endoscope image) only at the same respiration phase (or period around the same respiration phase) as the anatomic model. Likewise, the anatomic model at a particular stage of respiration may be matched and displayed with intraoperative fluoroscopic images only at the same respiration phase (or period around the same respiration phase) as the anatomic model.

At a process 722, the respiratory phase cycle data may be used to determine a robust parking location (i.e., location from which an auxiliary tool is deployed from the catheter) for the catheter from which the biopsy needle (or other auxiliary instrument) may be extended to conduct an interventional procedure such as a biopsy. The known motion of the airways may indicate (to a clinician or the control system) particular airways or locations within airways that may be more suitable than others for parking the catheter to perform the procedure such that the catheter does not become unexpectedly dislodged from its parked location due to the respiration cycle. Identifying a suitable parking location may be based upon the respiratory phase cycle data, but also may be determined from an anatomical atlas of the passageways or from the full inspiration/full expiration preoperative images.

Figure 10:
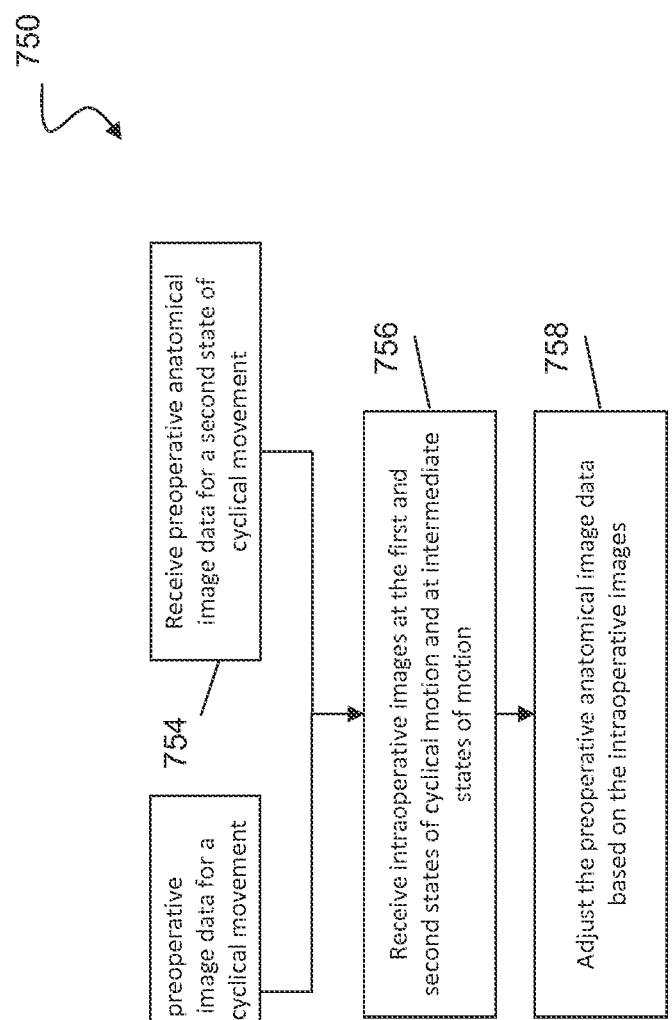
FIG. 10 illustrates a method of modifying preoperative anatomical image data based on intraoperative image data.

FIG. 10 illustrates a method 750 for adjusting an anatomic model or an anatomic image based upon intraoperative imaging. One or more of the processes 752-758 of the method 750 may be implemented, at least in part, in the form of executable code stored on non-transient, tangible, machine-readable media that when run by one or more processors may cause the one or more processors to perform one or more of the processes 752-758. At a process 702 anatomical image data from a preoperative anatomical image for first state of cyclical movement is received for processing. For example, if the anatomic cycle is respiration, a patient may be imaged at full inspiration, the state that corresponds to the first or maximum state of the cyclical movement. At a process 754 anatomical image data from a preoperative anatomical image for a second state of cyclical movement is received for processing. At a process 756, intraoperative images (e.g. fluoroscopic images) are obtained for the anatomy at the first state of cyclical movement (e.g., full inspiration) and at the second state of cyclical motion (e.g., full expiration). A set of images may also be obtained for states of cyclical movement between the first and second states. At a process 758, physical features may be identified in the intraoperative images that correspond to features in the preoperative images. Extracting a sufficient quantity and quality of features that correspond between the preoperative and intraoperative images allows the preoperative images to be adjusted in size, scale, orientation, and/or position based upon the intraoperative images. For example, the top-to-bottom size of the images for the preoperative state may be measured and scaled to the intraoperative images so that intermediate states of the preoperative images may be generated that follow and depict the motion of the intraoperative intermediate images.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A medical system comprising:
    an interventional instrument; and
    a control system including one or more processors, the control system configured to:
       receive a pose dataset for an identified point on the interventional instrument retained within and in compliant movement with a cyclically moving patient anatomy for a plurality of time parameters during a cyclical anatomical motion;
       determine a set of pose differentials for the identified point with respect to a reference point at each of the plurality of time parameters;
       identify a periodic signal for the cyclical anatomical motion from the set of pose differentials;
       generate a command signal indicating an intended movement of the interventional instrument relative to the patient anatomy;
       adjust the command signal to include an instruction for a cyclical instrument motion of the interventional instrument based on a phase of the cyclical anatomical motion indicated by the periodic signal; and
       cause the intended movement of the interventional instrument relative to the patient anatomy based on the adjusted command signal to compensate for the cyclical anatomical motion.

2. The medical system of claim 1 wherein the control system is further configured to:
    identify a first time parameter from the plurality of time parameters for the periodic signal, the first time parameter associated with a first distinct anatomic state.

3. The medical system of claim 2 wherein the control system is further configured to:
    identify a second time parameter from the plurality of time parameters for the periodic signal, the second time parameter associated with a second distinct anatomic state.

4. The medical system of claim 1 wherein the control system is configured to determine the set of pose differentials for the identified point by determining a displacement of the identified point with respect to the reference point at each of the plurality of time parameters.

5. The medical system of claim 1 wherein the control system is configured to determine the set of pose differentials for the identified point by determining a change rate of a displacement of the identified point with respect to the reference point at each of the plurality of time parameters.

6. The medical system of claim 5 wherein the control system is configured to identify the periodic signal for the cyclical anatomical motion by determining a sign change for the change rate of the displacement between two time parameters in the plurality of time parameters.

7. The medical system of claim 1 wherein the control system is configured to receive the pose dataset for the identified point by receiving the pose dataset from a shape sensor positioned within the interventional instrument.

8. The medical system of claim 1 wherein the control system is configured to receive the pose dataset for the identified point by receiving the pose dataset from an electromagnetic sensor positioned within the interventional instrument.

9. A non-transitory machine-readable medium storing instructions that, when executed by one or more processors, cause a control system to:
    receive a pose dataset for an identified point on an interventional instrument retained within and in compliant movement with a cyclically moving patient anatomy for a plurality of time parameters during a cyclical anatomical motion;
    determine a set of pose differentials for the identified point with respect to a reference point at each of the plurality of time parameters;
    identify a periodic signal for the cyclical anatomical motion from the set of pose differentials;
    generate a command signal indicating an intended movement of the interventional instrument relative to the patient anatomy;
    adjust the command signal to include an instruction for a cyclical instrument motion of the interventional instrument based on a phase of the cyclical anatomical motion indicated by the periodic signal; and
    cause the intended movement of the interventional instrument relative to the patient anatomy based on the adjusted command signal to compensate for the cyclical anatomical motion.

10. The non-transitory machine-readable medium of claim 9 further storing instructions that, when executed by one or more processors, cause the control system to:
    identify a first time parameter from the plurality of time parameters for the periodic signal, the first time parameter associated with a first distinct anatomic state.

11. The non-transitory machine-readable medium of claim 10 further storing instructions that, when executed by one or more processors, cause the control system to:
    identify a second time parameter from the plurality of time parameters for the periodic signal, the second time parameter associated with a second distinct anatomic state.

12. The non-transitory machine-readable medium of claim 9 wherein the instructions cause the control system to determine the set of pose differentials for the identified point by determining a displacement of the identified point with respect to the reference point at each of the plurality of time parameters.

13. The non-transitory machine-readable medium of claim 9 wherein the instructions cause the control system to determine the set of pose differentials for the identified point by determining a change rate of a displacement of the identified point with respect to the reference point at each of the plurality of time parameters.

14. The non-transitory machine-readable medium of claim 13 wherein the instructions cause the control system to identify the periodic signal for the cyclical anatomical motion by determining a sign change for the change rate of the displacement between two time parameters in the plurality of time parameters.

15. The non-transitory machine-readable medium of claim 9 wherein the instructions cause the control system to receive the pose dataset for the identified point by receiving the pose dataset from a shape sensor positioned within the interventional instrument.

16. The non-transitory machine-readable medium of claim 9 wherein the instructions cause the control system to receive the pose dataset for the identified point by receiving the pose dataset from an electromagnetic sensor positioned within the interventional instrument.

\* \* \* \* \*

UNITED STATES PATENT AND TRADEMARK OFFICE
CERTIFICATE OF CORRECTION

PATENT NO. : 11,723,606 B2
APPLICATION NO. : 17/127888
DATED : August 15, 2023
INVENTOR(S) : Prashant Chopra et al.

It is certified that error appears in the above-identified patent and that said Letters Patent is hereby corrected as shown below:

In the Specification

Column 1, Line 16, change "entire" to -- entirety --

Column 2, Line 26, change "passageway's" to -- passageways --

Column 3, Line 67, change "instalment" to -- instrument --

Column 4, Line 42, change "sob" to -- sub --

Column 10, Line 51, change "dine" to -- time --

Column 14, Line 59, after "at" add -- Pt-1st --

Signed and Sealed this
Third Day of October, 2023

*Katherine Kelly Vidal*

Katherine Kelly Vidal
*Director of the United States Patent and Trademark Office*